United States Patent [19]
Norton

[11] Patent Number: 5,920,916
[45] Date of Patent: Jul. 13, 1999

[54] URINE COLLECTION FUNNEL

[75] Inventor: Ian Fredric Norton, Toronto, Canada

[73] Assignee: G.D. Searle & Co., Chicago, Ill.

[21] Appl. No.: 08/809,302

[22] PCT Filed: Sep. 27, 1995

[86] PCT No.: PCT/US95/12337

§ 371 Date: Mar. 14, 1997

§ 102(e) Date: Mar. 14, 1997

[87] PCT Pub. No.: WO96/09794

PCT Pub. Date: Apr. 4, 1996

[30] Foreign Application Priority Data

Sep. 28, 1994 [CA] Canada ........................................ 78411

[51] Int. Cl.⁶ .................................................. A47K 11/00
[52] U.S. Cl. .................................................. 4/144.3
[58] Field of Search ................... 4/144.1–144.4, 4/340; 604/329; 141/340; D24/122

[56] References Cited

U.S. PATENT DOCUMENTS

| | | | |
|---|---|---|---|
| 105,979 | 8/1870 | Price | 4/144.1 |
| D. 267,118 | 11/1982 | Burnett | D24/122 X |
| D. 269,378 | 6/1983 | Work | D24/122 |
| D. 274,469 | 6/1984 | Huang et al. | D24/54 |
| 1,657,975 | 1/1928 | Shiells . | |
| 2,703,670 | 3/1955 | Voight | 141/340 |
| 3,000,015 | 9/1961 | Hart | 4/144.1 |
| 3,161,891 | 12/1964 | Bauman | 4/110 |
| 3,473,172 | 10/1969 | Friedman et al. | 4/110 |
| 3,711,871 | 1/1973 | Sherin | 4/110 |
| 3,815,770 | 6/1974 | Gaula | 215/253 |
| 3,878,571 | 4/1975 | Seeley | 4/110 |
| 3,927,426 | 12/1975 | Geddes | 4/110 |
| 4,408,905 | 10/1983 | Ehrenkranz | 4/144.1 X |
| 4,559,649 | 12/1985 | Burnett | 4/144.1 |
| 5,129,892 | 7/1992 | McCarthy | 604/329 |

FOREIGN PATENT DOCUMENTS 1 443 060   7/1976   United Kingdom .

OTHER PUBLICATIONS

Sporty's Pilot Shop, "Lady J. Adapter", p. 73 (date unknown).

*Primary Examiner*—Charles E. Phillips
*Attorney, Agent, or Firm*—Fitzpatrick, Cella, Harper & Scinto

[57] ABSTRACT

A urine collection funnel has an upper saddle-shaped oval opening with a curled lip for comfortably and securely fitting against the pelvic area of a user and a lower circular opening adapted to be secured to a container. An enclosed symmetrical side wall joins the upper and lower openings and includes opposite sides having convex-shaped contour surfaces. The lower opening is surrounded by a multi-rim arrangement for leak-free attachment to a conventional bottle or container. A lid snap-fits onto the upper opening.

17 Claims, 3 Drawing Sheets

URINE COLLECTION FUNNEL

BACKGROUND OF THE INVENTION

1. Field of the Invention

This invention relates generally to a urine collecting device, and more particularly to a urine collection funnel for directing urine into a container.

2. Description of the Prior Art

Being able to collect urine conveniently is important in several medical contexts. Tests on an individual's urine can reveal important medical information, such as the presence of substances in the body or specific medical conditions such as gastric ulcers. And the disabled, such as bed-ridden patients or invalids, also require a convenient manner of collecting urine that does not require them to get to a toilet.

However, it is not always easy to collect urine, especially for a female. While a male can usually direct his urine flow into a container, such as a glass bottle or a plastic container, a female generally has a much more difficult time accurately directing the flow of her urine. Thus, females sometimes have difficulty filling a container without some spilling and/or splashing of urine.

In a hospital, urine samples are sometimes collected using what is known as a "hat" because it resembles an upside down hat with a wide brim and a crown that is open at the top. The "brim" sits on the rim of a toilet under the toilet seat. After the patient urinates into the container formed by the open crown, the urine is emptied into a container for storage, testing or disposal. For bed-ridden or otherwise non-ambulatory patients in a hospital, a bed pan can be used instead of a hat. However, these devices, not being easily stored and readily portable, are not particularly convenient or practical outside a hospital or doctor's office. These devices may also experience spillage or contamination in transferring the urine into a container.

There are known in the art many different kinds of portable devices for collecting urine. Typically, such a device includes a funnel for receiving the urine and a detachable container for collecting and, if necessary, transporting the urine. Examples of urine collectors are shown in U.S. Pat. No. 1,657,975 (Shiells), No. 3,161,891 (Bauman), No. 3,473,172 (Friedman et al.), No. 3,927,426 (Geddes) and No. 4,559,649 (Burnett). Those patents disclose funnels with top edges that fail to properly fit the anatomy of a user, and thus are not particularly suitable for fitting against the pelvic region of an individual, particularly a female. Moreover, the funnel and detachable containers of these patents are not provided with adequate means for preventing or limiting leakage and/or spillage. The overall result of such conventional designs is that these urine collection devices can experience splashing and/or spilling of the urine as it is deposited into the funnel and drains into the container.

It is also known to design urine collection funnels to prevent leaking or contamination by the urine as it drains into an attached container. For example, U.S. Pat. No. 3,711,871 (Sherin) and No. 3,878,571 (Seeley) show urine collection devices with a bottom portion having a U-shaped channel for fitting over a lip of a urine collecting container. However, such conventional designs are still capable of leaking urine and contaminating the urine container and/or the urine sample.

It is desirable, therefore, to provide an improved device for collecting urine. The device should be simple, effective and convenient to use, for women as well as men, and also be inexpensive and sufficiently portable and easily stored to be practical for the home, as well as in professional medical settings.

SUMMARY OF THE INVENTION

It is a principal object of the invention to provide an improved urine collection device that can assist in collecting the urine of an individual.

Accordingly, it is an object of the present invention to provide a urine collection funnel for directing, or funnelling, urine from an individual into a urine collector.

It is another object of the present invention to provide a urine collection funnel that is convenient and comfortable to use by women and men, provides smooth urine flow and prevents back-splash of the urine.

It is still another object of the present invention to provide a urine collection funnel that can be used by individuals regardless of their physical condition, e.g., arthritic, infirmed, etc., or their position, e.g., standing, squatting, seated in a wheel chair, lying in bed, etc.

It is yet another object of the present invention to provide a urine collection funnel that can be secured to a urine collector and prevent leaking of urine as it drains from the funnel into the urine collector.

In accordance with one aspect, the present invention comprises a urine collection funnel with an inner surface terminating in a first opening for accepting urine from an individual into the funnel and a second opening adapted to direct the urine out of the funnel. The first opening is preferably an oval shape with a central axis and is symmetrical about an elongated axis intersecting the central axis, with the oval-shaped first opening shaped, for example, with a saddle-like contour, to fit the pelvic area of the individual. The inner surface proximate to the first opening has first and second opposing sides intersecting a plane defined by the elongated axis and the central axis, and the first and second opposing sides are symmetrical about the central axis and have a convex contour relative thereto, i.e., viewing the first and second opposing sides from inside the funnel.

In accordance with another aspect of the invention, a urine collection funnel comprises a urine collection funnel with an inner surface terminating in a first opening for accepting urine from an individual into the funnel and a second opening for directing urine from the funnel into a container, and securing means for securing the funnel to such a container to inhibit leakage of urine being transferred to the container from the funnel. The securing means comprises an outer rim having an inner surface for attachment to a urine accepting opening of the container, a guide ring forming with the outer rim a channel for accepting a rim of the urine accepting opening of the container, and an inner rim spaced inwardly from the guide ring and forming the inner surface of the funnel proximate to the second opening. The inner rim extends into the urine accepting opening of the container when the funnel is secured thereto to provide an annular space between an outer surface of the inner rim and an inner surface of the container opening.

These and other objects, aspects, features and advantages of the present invention will become apparent from the following detailed description of the preferred embodiments taken in conjunction with the drawings.

DESCRIPTION OF THE PREFERRED EMBODIMENTS

FIGS. 1 to 4 show a urine collection funnel 10 in accordance with a first embodiment of the invention. The funnel in this preferred embodiment is symmetrical about a central axis C and is formed basically of an enclosed side wall 12 extending from an upper portion 14 to a lower portion 16. As discussed in more detail below, the side wall provides a smooth inner surface terminating in an elongated, contoured oval-shaped first opening at the upper portion and a circular second opening at the lower portion.

Figure 1:
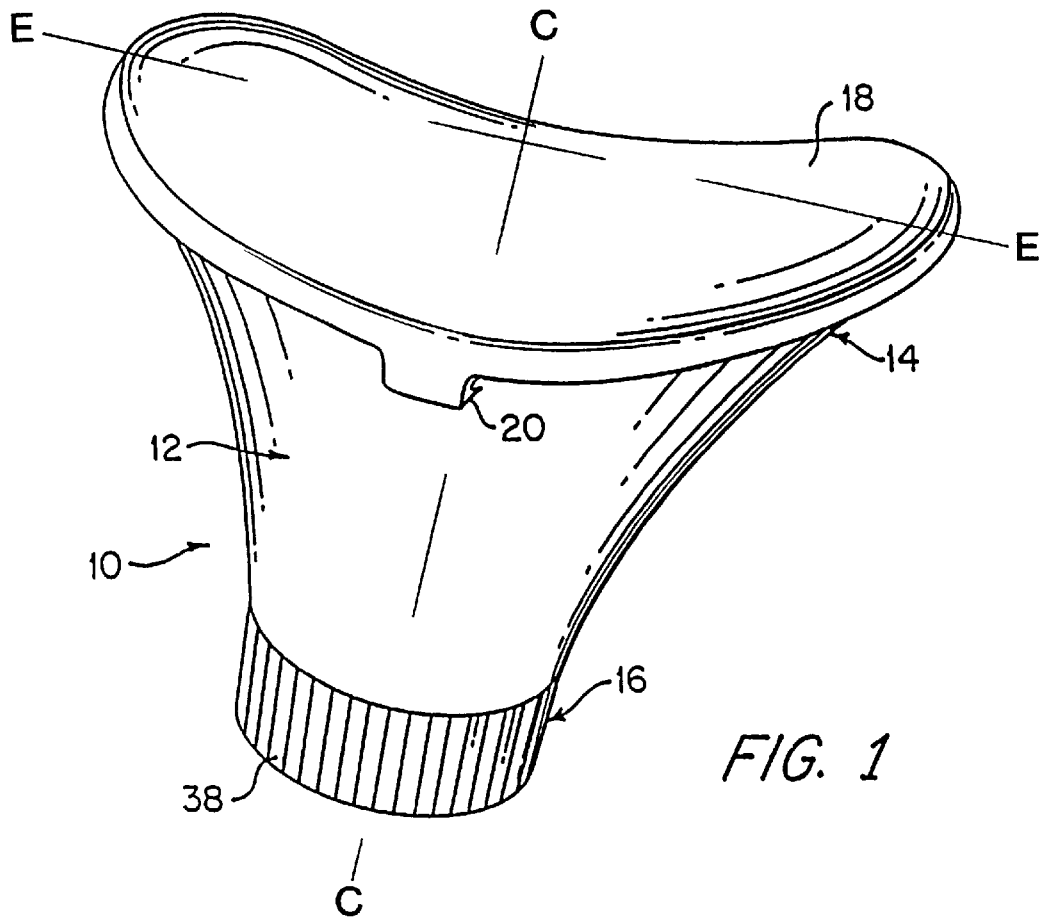
FIG. 1 is a perspective view of a urine collection funnel in accordance with a first embodiment of the invention.

A lid 18 can also be provided for covering the oval-shaped first opening. The lid helps to contain odor in the funnel and reduces contamination. The lid is preferably removable and, for that purpose, is provided with two snaps or clips 20 for securing it to an outwardly curled, down-turned lip 24 of a rim 22 shown in FIGS. 3 and 4. As seen in FIG. 1, the lid is oval-shaped and matches the contour of the first opening.

Figure 2:
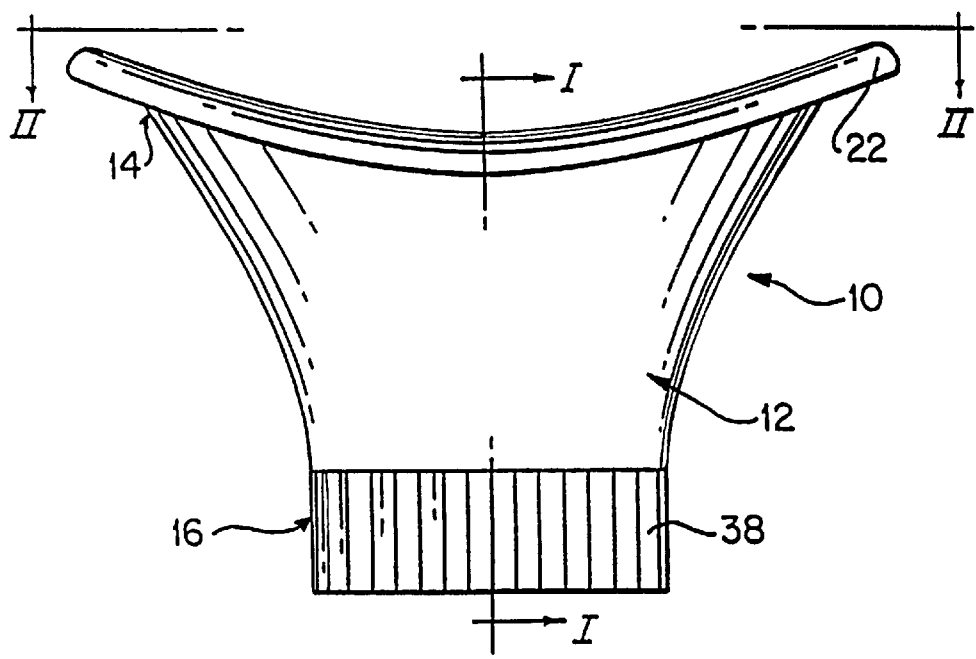
FIG. 2 is a side elevational view of the urine collection funnel shown in FIG. 1 without the lid.
Figure 4:
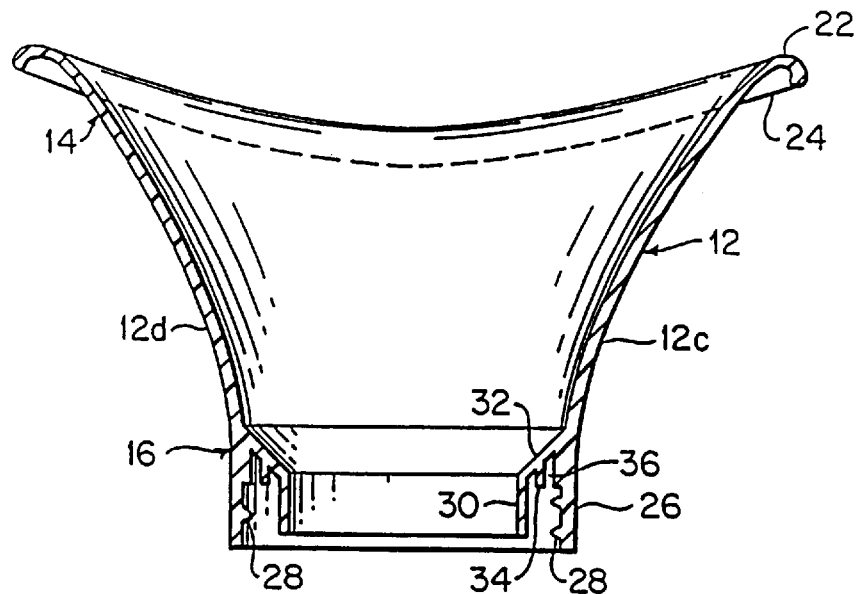
FIG. 4 is a cross-sectional view of the urine collection funnel taken along lines II—II of FIG. 2.
Figure 3:
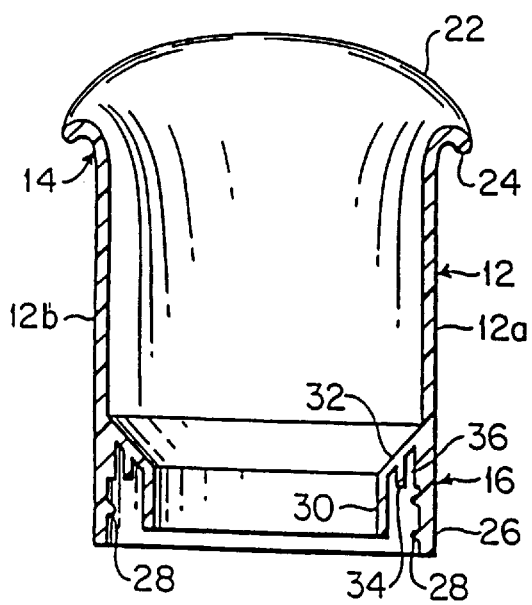
FIG. 3 is a cross-sectional view of the urine collection funnel taken along lines I—I of FIG. 2.

Details of the enclosed side wall 12 are best seen in the side view of FIG. 2 and the cross-sectional views of FIGS. 3 and 4. Generally speaking, the side wall is shaped so that the upper portion can fit comfortably between the legs and against the pelvic region of a user with a conventional bottle or other container for receiving the urine, which is attached to the second opening at the lower portion 16.

As is shown in FIG. 3, the funnel as seen from cross-section lines I—I in FIG. 2 has a relatively narrow width for fitting between the individual's legs. In this cross-section, the upper portion 14 and the lower portion 16 have substantially the same width. The rim 22 is formed at the top of the upper portion and terminates in the down-turned lip 24. As this cross-section also shows, opposite lateral sides 12a and 12b of the side wall 12 extend substantially parallel between the upper and lower portions.

The first opening at the top of the funnel is an oval shape symmetrical about a central axis that, in a preferred embodiment, coincides with the central axis C of the funnel. The oval shape of the first opening has an elongated axis E running lengthwise across the oval at its widest point and, thus, intersecting its central axis. Together those axes form a central plane P at which is taken the cross-sectional view shown in FIG. 4.

As seen particularly well in FIGS. 2 and 4, the rim 22 on the first opening is formed in a saddle-like contour to fit securely against the pelvic region of the user. The down-turned lip 24 increases the comfort afforded by the funnel, as well as enabling more secure contact with the user's body.

As seen in FIG. 4, opposite front and back sides 12c and 12d of the side wall 12 (that is, the sides that intersect the plane of FIG. 4) have a convex contour relative to the central axis C. The convex shape of the front and back sides 12c and 12d allow the urine to be deposited in the funnel with little or no splashing and smoothly drain toward the bottom portion.

The symmetrical oval shape and saddle-like contour of the first opening are important features of the present invention because they cooperate to provide the opening with no "front" or "back" side, and will fit equally well against the user's body regardless of the way it is oriented. This means that the funnel can be used more easily in the dark, or by patients who can become confused, and is particularly useful under these conditions by females. In addition, symmetrically designing the funnel to provide opposite sides 12c and 12d with the same flared contour allows the advantages of the convex contours of those sides to be realized when the funnel is used in either position, that is, one of the front and back sides of the funnel is always positioned in front of the user. Since both sides 12c and 12d are flared, urine directed to either side will be smoothly directed downwardly. That is, the shape and symmetry of the first opening and the front and back sides 12c and 12d proximate to the front opening provide a urine collection funnel that is equally effective in fitting the user and providing an anti-back splash feature that eliminates, or at least reduces, splashing and spilling of the urine, regardless of its orientation in use.

The lower portion 16 provides means for securing the funnel to a bottle or container for receiving the urine. As shown in both FIGS. 3 and 4, an outer rim 26 is formed at the terminal end of the side wall 12 and preferably has screw threads 28 at its internal surface for receiving a threaded opening of the bottle.

A concentric inner rim 30 of a smaller diameter than the outer rim extends downwardly from an angled surface 32 of the side wall 12. Between the inner and outer rims is a concentric guide ring 34. An annular channel 36 is formed between the guide ring 34 and the outer rim 26 for receiving the urine collecting bottle. As urine drains down the inner rim 30 and into the bottle, there will be no wicking of the urine toward the outer rim 26 or the mouth of the bottle because of the annular space between the outer surface of the inner rim and the inner surface of the opening of the bottle. Even if the bottle fills with urine, i.e., when the level of urine in the bottle reaches the inner rim, the shorter length of the guide ring 34 compared to the inner rim will inhibit wicking of the urine by capillary action because the urine will still remain out of contact with the guide ring 34 and the outer rim. In this manner, leaking of the urine or contamination of the urine or the bottle is effectively prevented.

One example of a container with a conventional opening that can be attached to the urine collection funnel of the present invention is disclosed in U.S. Pat. No. 5,226,551 (Robbins). That patent relates to a reusable and re-collapsible container that includes an exteriorly threaded portion at its mouth. When the mouth is properly inserted in the annular channel 36 of the lower portion, the inner rim 30 fits inside the mouth of the bottle without contacting the bottle to ensure leak-free flow of urine.

The urine collection funnel of the present invention is preferably a single piece molded from conventional plastic such as, for example, polypropylene. As shown in FIGS. 1 and 2, the exterior surface of the lower portion can be formed to have a ribbed or knurled surface 38 for easier gripping.

Figure 7:
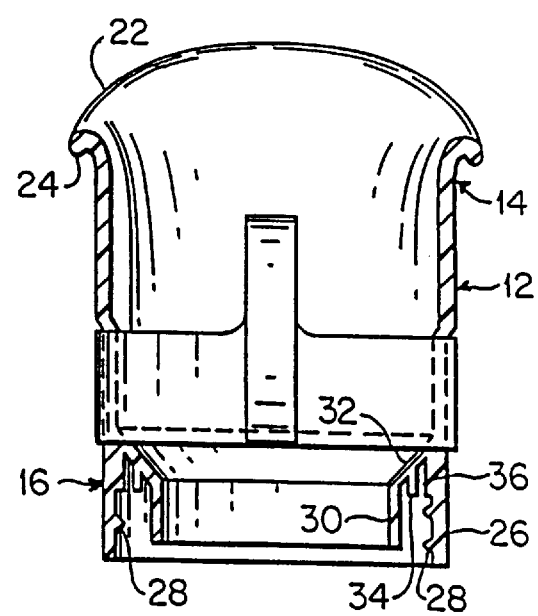
FIG. 7 is a side elevational view of the handle and a cross-sectional view of the urine collection funnel taken along lines III—III of FIG. 6.
Figure 5:
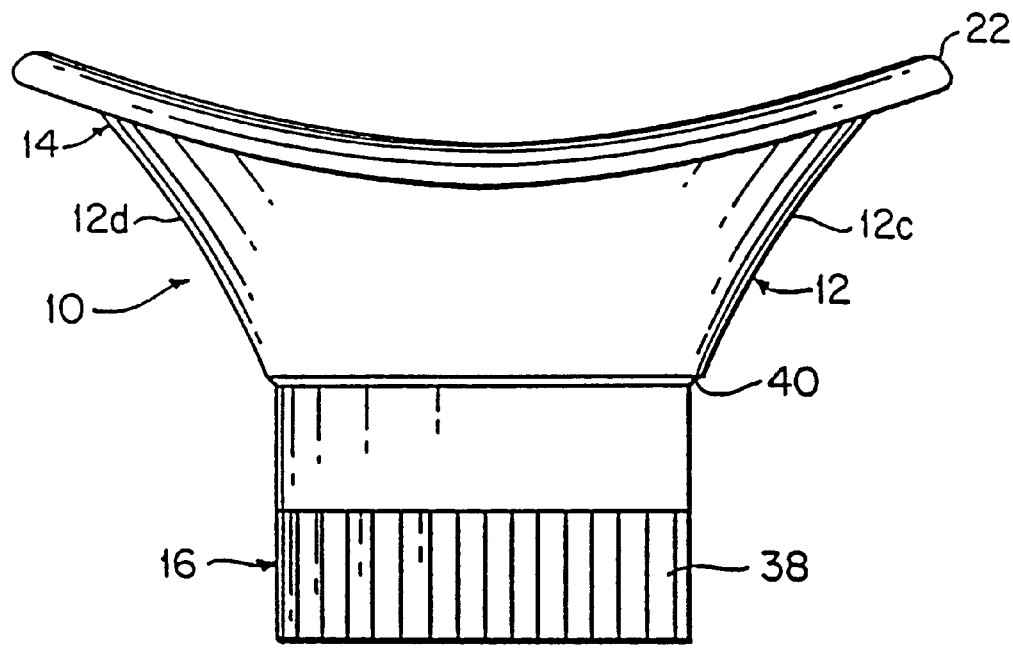
FIG. 5 is an elevational side view of the urine collection funnel in accordance with a second embodiment of the invention.
Figure 6:
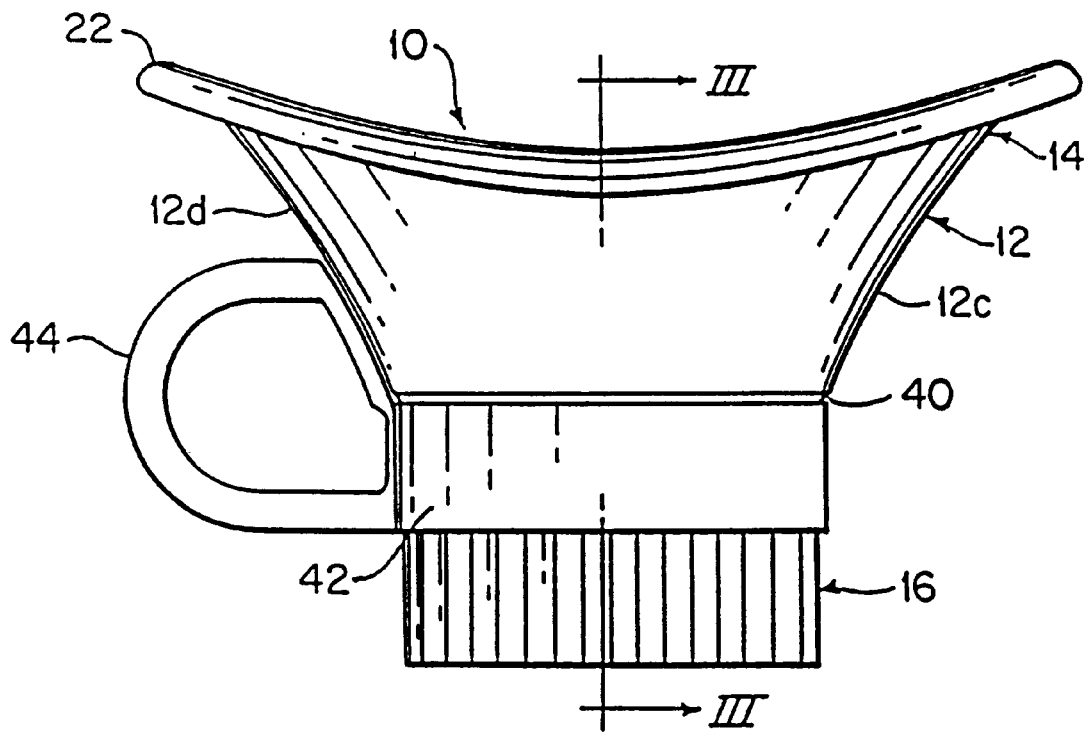
FIG. 6 is an elevational side view of the urine collection funnel shown in FIG. 4 with an optional handle.

A second embodiment of the present invention is shown in FIGS. 5 to 7. The second embodiment differs from the first embodiment described above only in that the front and back sides 12c and 12d of the side wall 12 taper inwardly from the upper portion 14 until approximately halfway down the side wall, at which point an upper ledge 40 is formed to encircle the side wall. As shown in FIG. 5, the portion of the side wall 12 from the upper ledge 40 to the lower portion 16 is substantially cylindrical and is dimensioned to match the lower portion. The front and back sides 12c and 12d have substantially the same flared contour as the front and back sides disclosed above with respect to the first embodiment and thus provide the same benefits and advantages.

By providing an upper ledge 40 on the exterior surface of the side wall 12, a carrying handle 42 can be used to support the funnel. In one embodiment, the handle is a closed circular loop and is slipped over the lower portion and rests against the upper ledge as shown in FIG. 6. In another non-limiting embodiment, the handle could be an open circular loop. The carrying handle includes a finger loop 44 for holding the funnel.

Other aspects of the funnel shown in the second embodiment are identical to the funnel described above with respect to the first embodiment and, thus, need not be further discussed.

In use, the urine collection funnel is secured to the urine collection bottle and then placed between the individual's legs and against the pelvic region. By virtue of the symmetrical design of the funnel, either the front or back sides can be positioned to face forward. Moreover, as discussed in detail above, the flared shape of both the front and back sides of the inner surface provides smooth urine flow and substantially prevents any back splashing of the urine. Still further, the lower portion of the funnel is secured to the collection bottle in a manner that prevents leaking of the urine and contamination of either the container or the urine itself, thus protecting the integrity of the urine sample. Another practical advantage of the invention is that, by providing outer and inner surfaces that have substantially the same configuration, storage space is minimized because the funnels will nest when stacked together.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A urine collection funnel with an inner surface terminating in a first opening for accepting urine from an individual into said funnel and a second opening adapted to direct the urine out of said funnel, wherein:

said first opening is an oval shape with a central axis and being symmetrical about an elongated axis intersecting said central axis, said oval-shaped first opening having a saddle-like contour for fitting the pelvic area of the individual;

said inner surface having first and second opposing lateral sides extending between said first and second openings, said first and second opposing sides being symmetrical about said central axis and having a convex contour portion relative to said central axis; and securing means for securing said second opening to a container, wherein said securing means includes a concentric inner rim and outer rim surrounding said second opening, and a concentric guide ring disposed between said inner and outer rims such that a container secured to said lower portion is received between said outer rim and said guide ring.

2. A urine collection funnel according to claim 1, wherein said second opening is circular.

3. A urine collection funnel according to claim 1, wherein said inner surface is a smooth curved surface and is symmetrical in all directions relative to said central axis.

4. A urine collection funnel according to claim 3, wherein said convex contour portion of said opposing sides extends substantially from said first opening to said second opening.

5. A urine collection funnel according to claim 3, wherein said convex contour portion of said opposing sides extends from said first opening and terminates approximately halfway to said second opening.

6. A urine collection funnel according to claim 5, further comprising an outer surface having a circumferential ridge formed at a location proximate to a terminal portion of said convex contour of said opposing sides, and further comprising a handle having a finger loop and a supporting rim for receiving said circumferential ridge and supporting said funnel.

7. A urine collection funnel according to claim 3, wherein said inner surface further includes third and fourth opposing sides extending substantially parallel to each other from said first opening to said second opening.

8. A urine collection funnel according to claim 1, wherein said outer rim includes screw threads on an inner surface thereof.

9. A urine collecting funnel according to claim 1, wherein said first opening includes an outwardly curled, down-turned lip.

10. A urine collecting funnel according to claim 9, further comprising a lid with clips for detachably securing said lid to said curled lip to cover said first opening.

11. A urine collecting funnel according to claim 1, further comprising a lid having means for detachably securing said lid to said funnel to cover said first opening.

12. A urine collection funnel with an inner surface terminating in a first opening for accepting urine from an individual into said funnel and a second opening for directing urine from said funnel into a container, and securing means for securing said funnel to such a container to inhibit leakage of urine being transferred to the container from said funnel, said securing means comprising:

an outer rim having an inner surface for attachment to a urine accepting opening of the container;

a guide ring forming with said outer rim a channel for accepting a rim of the urine accepting opening of the container; and an inner rim spaced inwardly from said guide ring and forming said inner surface of said funnel proximate to said second opening, wherein said inner rim extends into the urine accepting opening of the container when said funnel is secured thereto to provide an annular space between an outer surface of said inner rim and an inner surface of the container opening.

13. A urine collecting funnel according to claim 12, wherein said outer rim is circular and includes screw threads on said inner surface thereof for screwing onto the container opening and said outer rim, said guide ring and said inner rim are concentric.

14. A urine collecting funnel according to claim 12, wherein:

said first opening is an oval shape with a central axis and being symmetrical about an elongated axis intersecting said central axis, said oval-shaped first opening having a saddle-like contour for fitting the pelvic area of the individual; and said inner surface having first and second opposing lateral sides extending between said first and second openings, said first and second opposing sides being symmetrical about said central axis and having a convex contour portion relative to said central axis.

15. A urine collecting funnel according to claim 12, wherein said first opening includes an outwardly curled, down-turned lip.

16. A urine collecting funnel according to claim 15, further comprising a lid with clips for detachably securing said lid to said curled lip to cover said first opening.

17. A urine collecting funnel according to claim 15, wherein said outer rim is circular and includes screw threads on said inner surface thereof for screwing onto the container opening and said outer rim, said guide ring and said inner rim are concentric.

\* \* \* \* \*